United States Patent
Anderson et al.

(10) Patent No.: US 8,398,264 B2
(45) Date of Patent: Mar. 19, 2013

(54) LIGHTING DEVICE

(75) Inventors: John Anderson, Glasgow (GB);
Michelle MacLean, Glasgow (GB);
Scott John MacGregor, Glasgow (GB);
Gerald Alexander Woolsey, Glasgow (GB)

(73) Assignee: University of Strathclyde, Glasgow (GB)

( * ) Notice: Subject to any disclaimer, the term of this patent is extended or adjusted under 35 U.S.C. 154(b) by 410 days.

(21) Appl. No.: 12/739,802

(22) PCT Filed: Oct. 31, 2008

(86) PCT No.: PCT/GB2008/003679
§ 371 (c)(1),
(2), (4) Date: Apr. 26, 2010

(87) PCT Pub. No.: WO2009/056838
PCT Pub. Date: May 7, 2009

(65) Prior Publication Data
US 2010/0246169 A1    Sep. 30, 2010

(30) Foreign Application Priority Data
Oct. 31, 2007  (GB) .................................. 0721374.7

(51) Int. Cl.
*F21V 33/00* (2006.01)
*F21V 9/00* (2006.01)
(52) U.S. Cl. ......... 362/234; 362/231; 362/253; 362/276
(58) Field of Classification Search .................. 362/230, 362/231, 800, 234, 253, 276, 802, 804, 572–575
See application file for complete search history.

(56) References Cited

U.S. PATENT DOCUMENTS

| 3,992,646 | A | 11/1976 | Corth |
| 2003/0124023 | A1 | 7/2003 | Burgess et al. |
| 2004/0008523 | A1* | 1/2004 | Butler ........................... 362/551 |
| 2005/0055070 | A1 | 3/2005 | Jones et al. |
| 2005/0207159 | A1* | 9/2005 | Maxik ........................... 362/254 |
| 2006/0262545 | A1 | 11/2006 | Piepgras et al. |
| 2008/0008620 | A1* | 1/2008 | Alexiadis ......................... 422/24 |
| 2009/0034236 | A1* | 2/2009 | Reuben .......................... 362/103 |

FOREIGN PATENT DOCUMENTS

| EP | 1 693 016 A1 | 8/2006 |
| EP | 1 887 298 A1 | 2/2008 |
| JP | 2003-339845 A | 12/2003 |

(Continued)

OTHER PUBLICATIONS

Guffey et al., "Effects of Combined 405-nm and 880-nm Light on *Staphylococcus aureaus* and *Psuedomonas aeruginosa* in Vitro," *Photomedicine and Laser Surgery*, vol. 24, No. 6, 2006, pp. 680-683.
Guffey et al., "In Vitro Bactericidal Effects of 405-nm and 470-nm Blue Light," *Photomedicine and Laser Surgery*, vol. 24, No. 6, 2006, pp. 684-688.

(Continued)

*Primary Examiner* — Bao Q Truong
(74) *Attorney, Agent, or Firm* — Alston & Bird LLP

(57) ABSTRACT

A lighting device with at least one first-element that emits visible light at a wavelength and irradiance sufficient to inactivate one or more pathogenic bacterial species, and at least one second element that emits light of one or more longer wave-lengths to that of the first-element. The at least one second element has a higher illuminance than that of the at least one inactivating element or component.

30 Claims, 7 Drawing Sheets

FOREIGN PATENT DOCUMENTS

| | | |
|---|---|---|
| WO | WO-01/14012 A1 | 3/2001 |
| WO | WO-03/063902 A2 | 8/2003 |
| WO | WO-2004/033028 A2 | 4/2004 |
| WO | WO-2006/100303 A2 | 9/2006 |
| WO | WO-2006/126482 A1 | 11/2006 |
| WO | WO 2007/012875 A1 | 2/2007 |

OTHER PUBLICATIONS

Search Report from corresponding UK Patent Appl. No. GB0721374.7, dated Feb. 5, 2008.

International Search Report from corresponding International Appl. No. PCT/GB2008/003679, mailed Mar. 3, 2009.

\* cited by examiner (a) (b) (c)

LIGHTING DEVICE

The present invention relates to a lighting device for inactivating medically significant bacteria, such as methicillin-resistant *Staphylococcus aureus*, as well as a wide range of other problematic Gram positive and Gram negative bacteria.

BACKGROUND OF THE INVENTION

Methicillin-resistant *Staphylococcus aureus* (MRSA) and other Healthcare Associated Infections (HAIs) are an increasing problem for hospitals and medical clinics, and the healthcare industry is desperately seeking an effective solution for their prevention and control. HAIs are caused by pathogens that are transmitted through, for example, person-to-person contact and the shedding of skin scales. Existing methods of pathogen control involving hygiene are labour-intensive, difficult to monitor, and provide limited prevention and effectiveness.

Methods currently available for whole-room decontamination, such as UV-light, ozone and formaldehyde/ethylenoxide/hydrogen peroxide fumigation, cannot be used in the presence of people due to their toxicity. Therefore the area requiring decontamination must be sealed off and uninhabited during the process. Furthermore, these methods can have significant operator requirements for their application. Given the problems of MRSA and other HAIs, and the vast resources already committed to try to prevent and control them—without notable success—it is apposite to confront the challenge with a new approach.

WO 2007/012875 A1 describes a technique for inactivating various pathogenic Gram-positive bacteria. It involves exposing the pathogenic bacteria to visible light, preferably having a wavelength in the range of 400-500 nm, without using a photosensitiser. The bacteria that can be inactivated include *Staphylococcus*, in particular MRSA, Coagulase-Negative *Staphylococcus* (CONS), *Streptococcus, Enterococcus* and *Clostridium* species. By using light in the visible-wavelength region there is no detrimental effect on human or animal health, so that the method can be used in indoor environments for air disinfection, as well as for contact-surface and materials disinfection.

SUMMARY OF THE INVENTION

According to a first aspect of the invention, there is provided a lighting device with at least one first-element that emits visible light at a wavelength and irradiance sufficient to inactivate one or more pathogenic bacterial species, and at least one second illuminating element that emits light of longer wavelengths to that of the first-element, wherein the at least one second element has a higher illuminance than that of the at least one inactivating element or component. Preferably, the illumination element has an illuminance (in lux) that is at least three times the illuminance of the at least one inactivating element or component.

According to another aspect of the present invention, there is provided a lighting device that has at least one element or component, preferably an LED, that emits visible light at a wavelength and intensity sufficient to inactivate one or more pathogenic or potentially pathogenic bacteria such as methicillin-resistant *Staphylococcus aureus*, in the air and on contact surfaces and materials, and at least one other element or component, preferably an LED, that emits visible light at a different wavelength, the combined output of the device being white or a shade or white. The bacteria-inactivating LED may have a wavelength centred on 405 nm.

According to still another aspect of the invention, there is provided a lighting device with at least one first-element that emits visible light at a wavelength and intensity sufficient to inactivate one or more pathogenic bacterial species in the air and on contact surfaces and materials, and at least one second-element that emits light of different wavelengths to that of the first-element, wherein the at least one first bacteria-inactivating element is operable in a first mode to emit light having an irradiance in a first range, and in a second mode to emit light having an irradiance in a second, different range.

According to yet another aspect of the invention, there is provided a lighting device with at least one first-element that emits visible light at a wavelength and intensity sufficient to inactivate one or more pathogenic bacterial species, and at least one second-element that emits light of different wavelengths to that of the first-element, wherein the at least one second element is operable to provide environmental illumination.

By inactivation, it is meant that the bacteria are killed, or damaged so as to reduce or inhibit bacterial replication. The methods and systems can therefore be considered as bactericidal and/or bacteriostatic depending on the species/strain of bacterium, wavelength of light, dose, etc. By pathogenic or potentially pathogenic, it is meant bacteria capable of causing disease or infection in a human or animal subject.

The device of the present invention can be designed to disinfect the air and surfaces of indoor environments such as floors, desks, tables, bed clothes, curtains, blinds, etc that are present within the clinical or other area. There is no requirement for user involvement and pathogen inactivation is continuous. The light is complementary to existing prevention and control methods such as hand washes, wipes and disinfectants, and also tackles the unresolved problem of environmental transmission of micro-organisms.

The LED lighting device may include, in addition to the bacteria-inactivating, light component, at least one second element that is operable to emit light of a different wavelength within the visible spectrum. The combined light output of the LEDs of the LED lighting device is designed to produce light that is non-disturbing to personnel.

Each bacteria-inactivating or first-element LED, may emit light having a wavelength in the range 380 nm to 420 nm. The wavelength may be centred on 405 nm. The second-element LED(s) may be white or another colour that complements the violet of the 405 nm LED(s) to provide a combined output that is non-disturbing and easy on the eye.

A lens may be provided for directing light onto a target region. Additionally or alternatively, a diffuser may be provided for blending light from the first-element and second-element LEDs.

A plurality of the bacteria inactivating lights may be provided. The bacteria inactivating lights may all emit at the same wavelength. The bacteria inactivating lights may emit at different wavelengths.

A plurality of second lights may be provided. The second lights may all emit at the same wavelength. The second lights may each emit at different wavelengths. The second lights may emit white light. The second lights may emit light that is a shade of white.

The first-element lights may be operable to emit light having an irradiance in the range up to 0.50 mW/cm$^2$.

The first-element lights may be operable in a first mode to emit light having an irradiance in a first range, and in a second mode may have an irradiance that is greater than that in the first mode. The device may be such that in the first mode light is emitted from the at least one first-element in a range that allows it to be operated continuously in the presence of human beings or animals. The light emitted in the first mode may have an irradiance in the range up to 0.50 mW/cm². The light in the second mode may have an irradiance of more than 0.50 mW/cm².

Means may be provided for switching between the first and second modes. The means for switching may be responsive to the detection of a person. The means for switching may be responsive to the detection of movement. The means for switching may be responsive to a change in an environment such as the opening or closure of a door.

Means may be provided for varying the level of irradiance of the first and/or second-element LEDs.

BRIEF DESCRIPTION OF THE DRAWINGS

Various aspects of the present invention are described by way of reference in the accompanying drawings, of which.

DETAILED DESCRIPTION OF THE INVENTION

Figure 1:
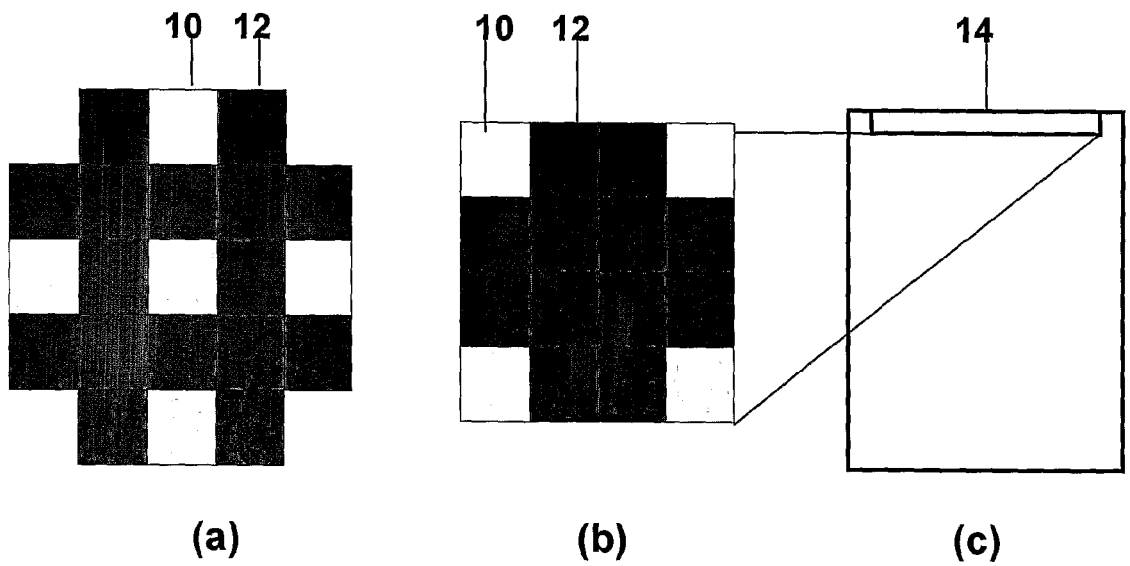
FIG. 1 shows plan views of two of the possible LED configurations of a lighting device for environmental control of pathogens, and one of these fitted inside an enclosure.

FIG. 1 shows examples of possible configurations for a lighting device that is operable to inactivate one or more pathogenic or potentially pathogenic bacteria, such as methicillin-resistant *Staphylococcus aureus*. Any chosen configuration is made up of a plurality of lights 10, typically LEDs, with a wavelength component in the range between 380 nm and 420 nm, for inactivating bacteria and a plurality of lights 12, again typically LEDs, that emit light that is white or a shade of white or light of colours outside the 380-420 nm range to alleviate any discomfort that might be experienced from the 405-nm light alone. The elements can be arranged on a single substrate in any desired pattern, as shown in FIGS. 1(a) and 1(b). The device can be used to simultaneously illuminate and decontaminate any area, for example the inside of an enclosure 14, as shown in FIG. 1(c).

The elements are arranged so that the integrated output of the device appears as white light a shade of white or a colour that is non-disturbing to personnel. This avoids the irritation that some people experience when exposed to light in the 380 nm to 420 nm range; that is, to violet light. The output of the light is such as to provide sufficient irradiance to inactivate infection-producing bacteria over a surface area of the order of square metres, as well as in the surrounding air.

Figure 4:
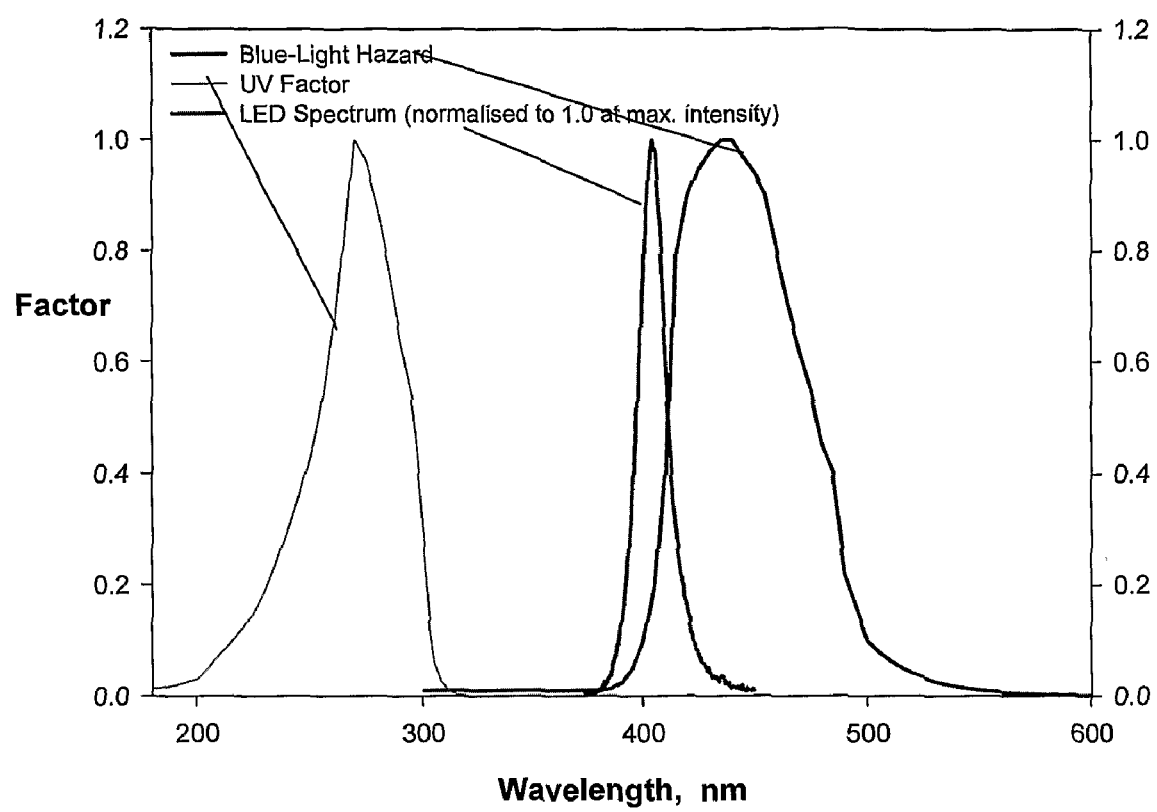
FIG. 4 shows plots of safety factors for UV and blue light as a function of wavelength, together with a normalised spectrum of the output of a 405-nm LED.
Figure 5:
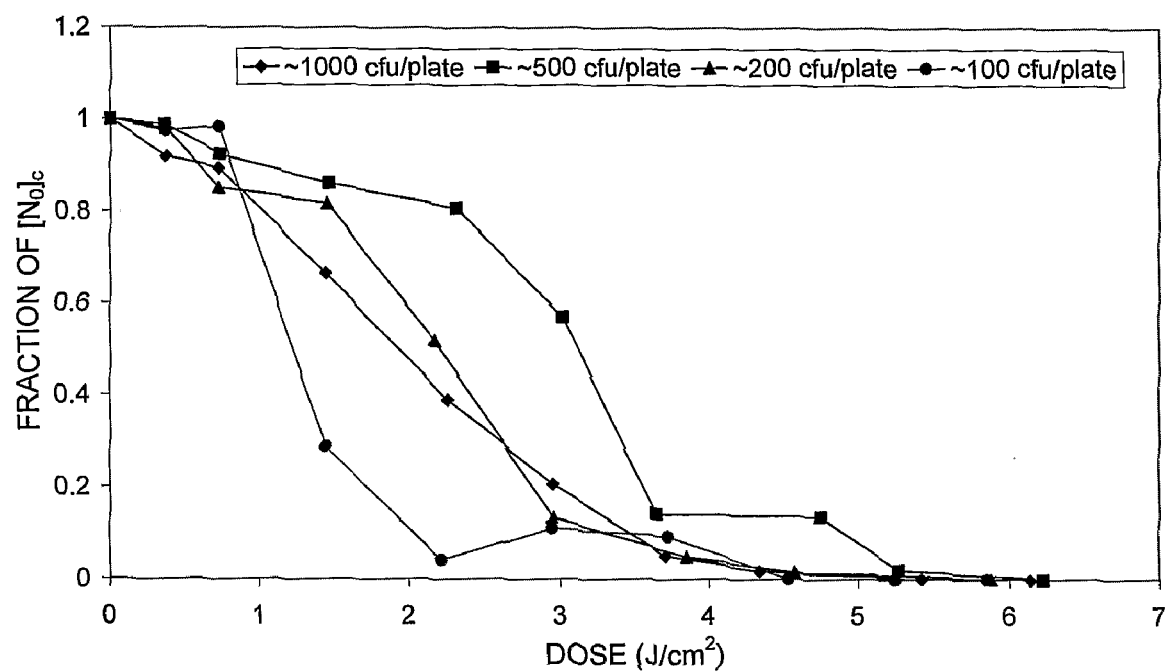
FIG. 5 shows normalised plots of bacterial counts of *Staphylococcus aureus* NCTC 4135 exposed to a 0.2 mW/cm² inactivating light as a function of dose.

In a preferred embodiment, the bacteria-inactivating LEDs produce light in a narrow wavelength range centred on 405 nm, as shown in FIG. 4. Light in this narrow wavelength range photo-excites intracellular molecules inducing the production of free-radical molecules, such as the highly reactive singlet oxygen, within the bacterial cells. The process occurs with maximum efficiency at 405 nm, and leads ultimately to irreversible inactivation of bacterial cells. The inactivating component of the lighting device is High-Intensity (high irradiance) and Narrow-Spectrum and so shall be referred to as a HINS light.

The LED lighting device of the invention can take different forms, provided that it includes the necessary active wavelength component with sufficient irradiance and its net light intensity is not disturbing to the eyes. The HINS-light LEDs will normally be in the form of 405 nm LEDs, chosen to provide irradiance (mW/cm²) over a surface area of several square metres that is sufficiently intense to inactivate bacteria in the air and on surrounding contact surfaces and materials to an acceptable low level in a period of hours without causing any distraction to the eyes. A typical level of continuous irradiance in a populated environment will be between 0.05 mW/cm² and 0.50 mW/cm². Because the eye is relatively insensitive to violet light, these values of irradiance appear relatively faint, corresponding to an illuminance of 2 to 6 lux. Normal room lighting is in the range 200-500 lux. However, even at these low levels of illuminance, violet light can lead to a degree of eyestrain, dizziness and headaches. To overcome this problem, the LED lighting device is arranged so that the added white light or light of other wavelengths dominates the overall output. By adding white light or light of other wavelengths with an illuminance of 2-3 times that of the violet light, a light source of 10-20 lux is obtained.

Figure 2:
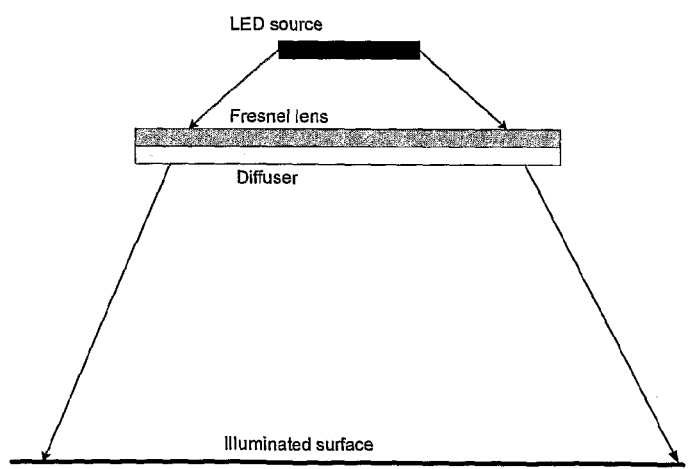
FIG. 2 is a side view of a possible configuration of the device for environmental control of pathogens.

FIG. 2 shows an example of an appropriate LED lighting device. It has a lens, such as a Fresnel lens, positioned to distribute the light in a controlled manner, and a diffuser to blend the violet and white or colour components of light more uniformly. The lens/diffuser diameter is 30 cm, so that a circular surface area of around 10 m² can be irradiated from a distance of 2.0 m with an average irradiance of 0.15 mW/cm². Table 1 provides the radiometric/photometric values for the violet (HINS-light) component of this 0.15 mW/cm² diffuse system.

TABLE 1

| HINS-light Radiometric | HINS-light Photometric |
|---|---|
| Radiant flux: 18 W | Luminous flux: 72 lumen |
| Radiant intensity: 6 W/sr | Luminous intensity: 25 candela |
| Irradiance: 1.5 W/m² | Illuminance: 6 lux |
| Radiance: 85 W/m²sr | Luminance: 348 cd/m² |

Figure 3:
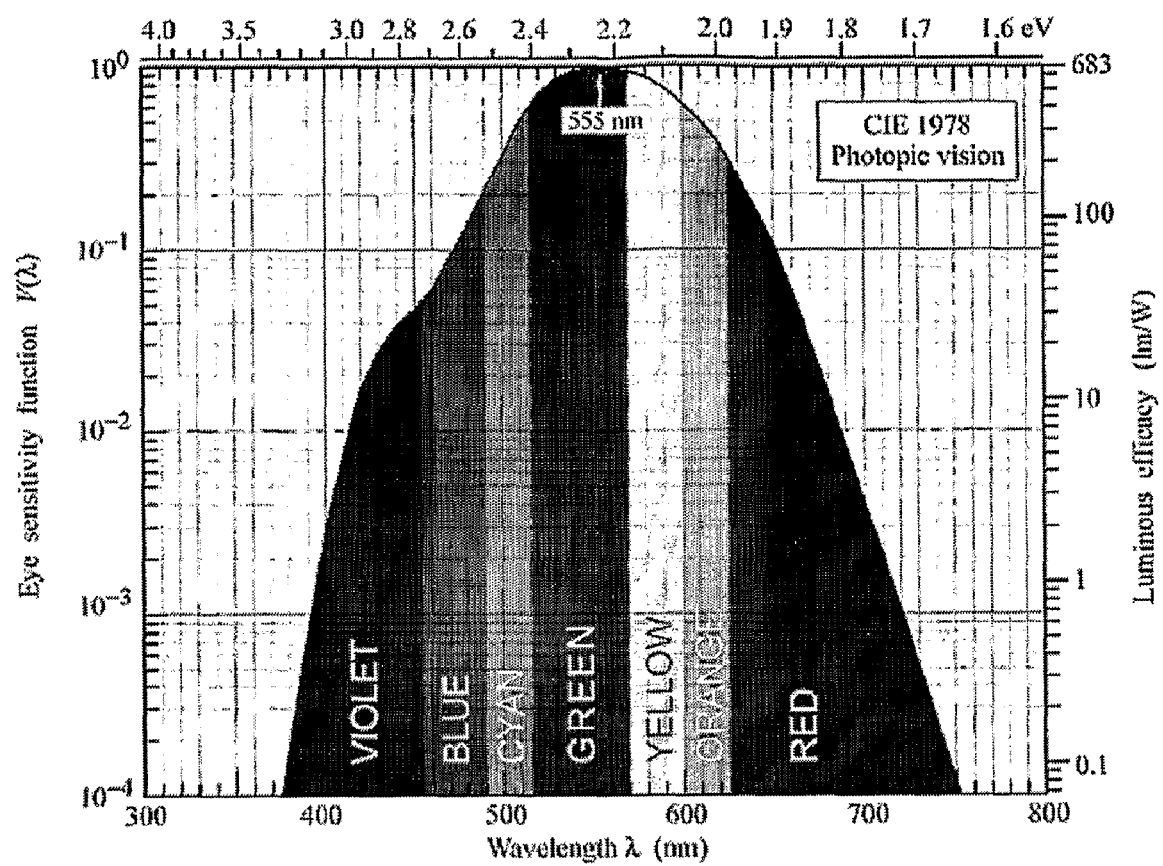
FIG. 3 is a plot of eye sensitivity function and luminous efficiency (lm/W) as a function of wavelength (after 1978 Commission Internationale de l'Eclairage data)

The radiometric quantities are the actual values of the electromagnetic radiation, while the photometric quantities are associated with the radiation that is detectable by the eye. More specifically, the photometric values are the radiometric values weighted by the eye sensitivity function. FIG. 3 shows the weighting factor, termed the luminous efficiency, as a function of wavelength.

FIG. 4 graphically displays the safety factors for UV and blue light obtained from the guidelines on limits to exposure of optical radiation provided by the International Commission on Non-Ionizing Radiation Protection (ICNIRP). The HINS-light spectral distribution is also displayed in FIG. 4, normalised to unity at the maximum for ease of comparison with the guideline safety factors. Much of the information provided by ICNIRP is taken from the work of the American Conference of Governmental Industrial Hygienists (ACGIH). The relevant publications are:

ICNIRP. *Guidelines on limits of exposure to optical radiation from 0.38 to 3.9 mm*. Health Physics 73; 539-554; 1997.

ICNIRP. *Guidelines on limits of exposure to ultraviolet radiation of wavelengths between 180 nm and 400 nm (incoherent radiation)*. Health. Physics 87, 171-186; 2004.

ACGIH. *Threshold Limit Values & Biological Exposure Indices*. Signature Publications, Cincinnati, 2007.

For HINS light, the important safety aspect that is likely to have most significance is that associated with blue-light injury to the retina of the eye. As can be seen in FIG. 4, there is some overlap between the HINS-light LED spectrum and the curve for the blue-light factor. Thermal and ultraviolet effects have also been considered. FIG. 4 provides an indication of the relative safety of HINS light with its spectrum falling between the peaks of the UV and blue-light factors, and this is borne out by the results of a detailed safety analysis. The detailed safety analysis uses the ICNIRP guidelines in conjunction with the HINS-light output data of Table 1, and the results obtained from the analysis show that the HINS-light component of the LED lighting device as specified is safe for operation in the presence of people. The safety factors for different interaction processes for this particular HINS-light component are listed in Table 2, as percentages of the TLVs (Threshold Limit Values) specified by ICNIRP/ACGIH.

TABLE 2

| Interaction Process | % TLV |
|---|---|
| Thermal → skin & eyes | negligible |
| UV → skin | negligible |
| UV → eyes | 4% |
| Blue-light → eyes | 20% |

Whilst the HINS-light LEDs can be operated below TLVs, in Mode I, during the day to ensure safety, they can be boosted overnight when personnel are no longer present, Mode II. For Mode II operation, the second-element LEDs of different wavelength used in the device to alleviate any discomfort experienced from the light of the HINS device are not required. Safety and discomfort are then no longer issues, and the level of irradiance is limited only by the specifications of the source. A similar approach can be applied, for example, to refrigerator or storage or cabinet lighting, where the door-closing switch that switches off the interior light can also be used to switch on an interior lighting device made up of HINS-light LEDs. The HINS light will provide a useful addition to the control of bacterial growth on the surfaces of foodstuffs. For a toilet cubicle, a lighting device made up of HINS-light LEDs that automatically switches on only when the cubicle is unoccupied will provide on-going disinfection, and again, the system can be operated in Mode II without reference to safety factors. Clean rooms, as used in the pharmaceutical industry, represent another environment in which the device can be operated in either Mode I or Mode II.

The LED lighting device of the present invention can be used to inactivate many different types of bacteria in the air and on contact surfaces and materials. Bacteria that may be inactivated include the following: *Staphylococcus aureus*, MRSA, coagulase-negative *Staphylococcus, Streptococcus, Enterococcus, Clostridium, Bacillus, Listeria, Acinetobacter, Pseudomonas, Klebsiella, Proteus, Salmonella* and *Escherichia*. All have shown susceptibility to HINS-light, indicating that its antimicrobial treatment is effective against an extensive range of both Gram-positive and Gram-negative bacteria.

To demonstrate the effectiveness of the device for inactivation of bacteria, several studies have been carried out. The bacteria examined were: *Staphylococcus aureus* NCTC 4135; *Staphylococcus epidermidis* NCTC 11964, *Clostridium difficile* NCTC 11204, *Acinetobacter baumannii* NCTC 12156, *Proteus vulgaris* NCTC CN 329, *Pseudomonas aeruginosa* NCTC 9009, *Klebsiella pneumoniae* NCTC 9633 and *Bacillus cereus* NCTC 11143. Samples of all bacteria, except *Clostridium difficile*, were serially diluted to the appropriate concentration using phosphate-buffered saline (PBS), plated out using Nutrient Agar (NA) and then incubated aerobically at 37° C. for 24 hours. For *Clostridium difficile*, the procedures used were the same except that bacteria were plated out on Blood Agar (BA) and incubated under anaerobic conditions at 37° C. for 48 hours.

FIGS. 5 to 8 show the results of inactivation of different bacterial samples using the LED lighting device of the present invention. In each example, the irradiance values quoted are those for the 405-nm centred, first-element, HINS-light component of the light. Furthermore, the quoted dose values in J/cm$^2$ are the product of this irradiance in W/cm$^2$ and the exposure time in seconds. Dose is the significant parameter for inactivation: in all inactivation experiments covering a wide range of bacteria, the level of inactivation is found to be dose dependent, meaning that, for a particular bacterium, a high irradiance for a short time has the same inactivating effect as a low irradiance for a long time, provided the dose values are the same. For the studies that provided the data in FIGS. 5 to 8, the second-element white-light component had an irradiance of 0.04 mW/cm$^2$. This value however is not important for bacterial inactivation. The irradiance of the white/coloured LEDs can have any value provided the illuminance in lux is such that the net light output from the lighting device is non-disturbing—this requires the white/coloured-LED component to have an illuminance (in lux) that is greater than that of the HINS light component, and typically at least three times the illuminance of the HINS-light component.

Suspensions of different concentrations of *Staphylococcus aureus* NCTC 4135 were prepared in PBS and equal aliquots of these were spread on the surface of Nutrient Agar plates to give plating densities of 100 colony forming units per plate (cfu/plate), 200 cfu/plate, 500 cfu/plate and 1000 cfu/plate. A number of plates with each plating density were then exposed to the LED lighting device. The HINS-light component was set to provide an irradiance value of 0.2 mW/cm$^2$ and plates were exposed for different exposure times to give a range of doses (irradiance×exposure time) extending from less than 1 J/cm$^2$ to greater than 6 J/cm$^2$. The results of these experiments are shown as normalised data in FIG. 5. From these, it can be seen that exposure of all the tested plating densities of *Staphylococcus aureus* NCTC 4135 to the LED lighting device resulted in a significant dose-related reduction of counts. As would be expected, plating density also had an effect with higher plating densities requiring a larger dose to achieve total inactivation.

In other experiments, *Staphylococcus aureus* NCTC 4135 suspensions were plated out onto Nutrient Agar plates and these were exposed to the LED lighting device with different levels of irradiance from the 405 nm centred, HINS-light component. The irradiance levels ranged from 0.005 mW/cm$^2$ to 0.5 mW/cm$^2$, as would be used in Mode I operation of the LED lighting device. Different exposure times were used; these being 6 hours, 8 hours and 16 hours. The reductions in *Staphylococcus aureus* counts (cfu/plate)

achieved by these treatment regimes are shown below in Table 3. The results are expressed as a reduction in cfu/plate and as a % reduction. As expected, both irradiance level and exposure time have an effect on *Staphylococcus aureus* inactivation. Even HINS-light irradiance at the lowest level of 0.005 mW/cm$^2$ for an exposure time of 8 hours caused a significant reduction in the *Staphylococcus aureus* cfu count, providing evidence of the significance of dose for inactivation.

TABLE 3

| Irradiance (mW/cm$^2$) | Exposure Time | Reduction (cfu/plate) | % Reduction |
|---|---|---|---|
| 0.5 | 18 h | ~1,000,000 → 1 | 99.999 |
| 0.2 | 18 h | ~1,000,000 → 130 | 99.987 |
| 0.15 | 6 h | 271 → 4 | 98.5 |
| 0.1 | 8 h | 407 → 11 | 97 |
| 0.05 | 8 h | 399 → 49 | 88 |
| 0.015 | 8 h | 207 → 39 | 81 |
| 0.005 | 8 h | 128 → 75 | 42 |

Figure 6:
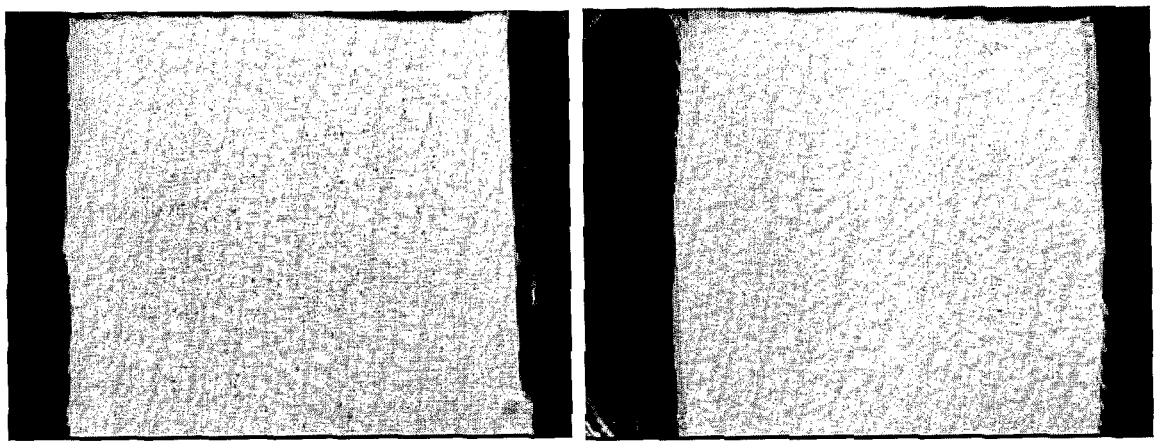
FIG. 6 shows a control sample on the left and a test sample on the right that demonstrates the inactivation of *Staphylococcus aureus* NCTC 4135 seeded on cotton fabric.

The effect of exposure of contaminated cotton fabric to light from the LED lighting device was also examined. Pieces of cotton fabric were contaminated by spreading on them a PBS suspension of *Staphylococcus aureus* NCTC 4135 cells. A piece of contaminated fabric was then exposed to a HINS-light irradiance level of 5 mW/cm$^2$ for 50 min (resulting in a dose of 15 J/cm$^2$) and a non-exposed piece of fabric served as a control. After exposure, both pieces of cotton fabric were overlayed with Nutrient agar (NA) containing Triphenyltetrazolium chloride (TTC) and left to solidify, before being placed under incubation conditions. Due to the presence of TTC in the culture medium, any surviving *Staphylococcus aureus* cells developed as red coloured colonies on the fabric. The appearance of the exposed and non-exposed pieces of fabric is shown in FIG. 6. The control sample (non-exposed) that is impregnated with red-coloured *Staphylococcus aureus* colonies is shown on the left and the exposed sample without colonies is shown on the right.

Figure 7:
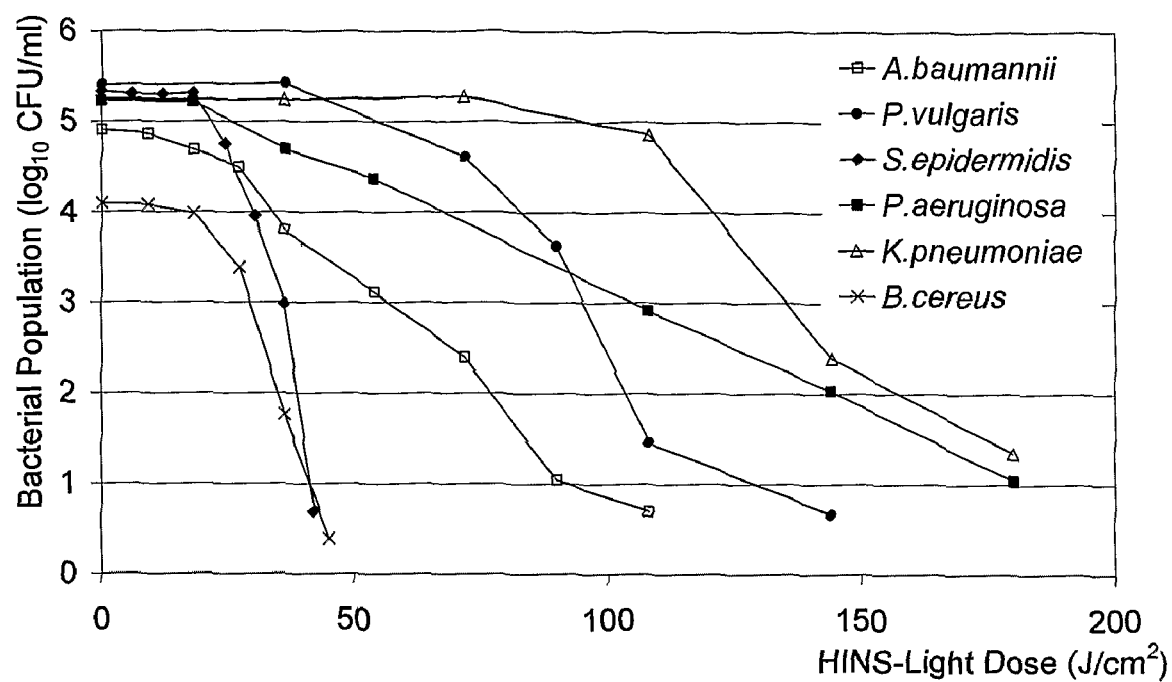
FIG. 7 shows plots of bacterial counts as a function of dose in suspensions of different bacteria exposed to light from a 405 nm centred LED array.

The effectiveness of the HINS-light component of the LED lighting device for the inactivation of a wide range of different types of bacteria was examined. Liquid PBS suspensions of the following bacteria were prepared: *Acinetobacter baumannii* NCTC 12156, *Proteus vulgaris* CN 329, *Staphylococcus epidermidis* NCTC 11964, *Pseudomonas aeruginosa* NCTC 9009, *Klebsiella pneumoniae* NCTC 9633 and *Bacillus cereus* NCTC 11143. The test suspensions were exposed to light from the LED lighting device with a 405 nm centred, HINS-light component at an irradiance level of approximately 10 mW/cm$^2$ for increasing time periods. Inactivation curves of the different bacteria are shown in FIG. 7, plotted as HINS-light dose as a function of bacterial population. The dose was calculated from the irradiance×exposure time. From FIG. 7 it can be seen that the HINS-light component of the LED lighting device caused a significant reduction in the cfu counts of all the bacteria tested. The results also show that different types of bacteria exhibit different degrees of susceptibility to the inactivating HINS light. The results illustrate that, regardless of differences in comparative susceptibility, reductions of 4 to 5 log orders were achieved with all tested bacteria.

Figure 8:
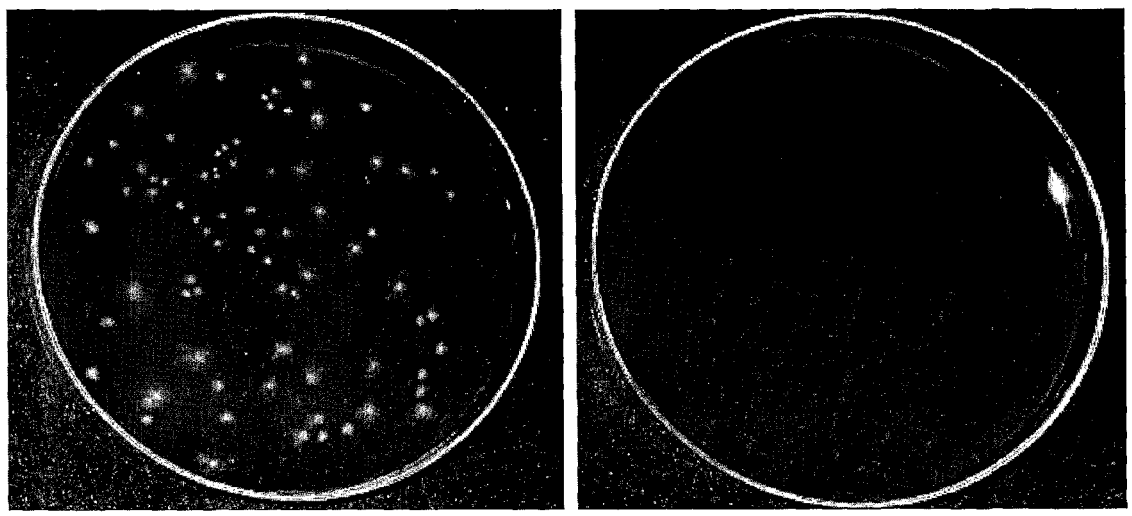
FIG. 8 is a visual indication of the inactivation of *Clostridium difficile* NCTC 11204 caused by exposure to light from a 405 nm centred LED array.

*Clostridium difficile* is an extremely important hospital pathogen and tests were carried out to find out if this pathogen could be inactivated by exposure to the LED lighting device. *Clostridium difficile* NCTC 11204 was cultured under anaerobic conditions and a suspension of cells prepared in phosphate buffered saline (PBS). The cell suspension was then exposed to the LED lighting device with a 405 nm centred, HINS-light component of approximately 40 mW/cm$^2$ irradiance for 10 min. The suspension was then plated onto Blood Agar (BA) and incubated under anaerobic conditions at 37° C. for 48 hours. A visual indication of the inactivation of *Clostridium difficile* by exposure to the HINS-light component is shown in FIG. 8. The BA plate inoculated with the control (non-illuminated) suspension (showing extensive growth of *Clostridium difficile* colonies) is shown on the left and the BA plate inoculated with the HINS-light treated suspension (showing no *Clostridium difficile* colonies) is shown on the right. Although this exposure was carried out using a HINS-light component as used in a Mode II device (40 mW/cm$^2$ irradiance), the same result could be obtained using the device in Mode I, with for example, a 0.5 mW/cm$^2$ HINS-light component and an exposure time of 800 min. The dose in the two cases is the same, namely 24 J/cm$^2$.

The decontamination light described here is strongly bactericidal, yet safe for humans. It inactivates pathogens using high intensity, narrow spectrum light within the visible spectrum and typically centred on a wavelength of 405 nm. This unique feature facilitates its application for continuous decontamination of clinical areas whilst being operated in the presence of patients and staff, as well as any inhabited area in the home, office, shopping centre, etc.

The LED lighting device of the present invention can be readily operated in the presence of people, is safe, non-obtrusive and does not rely on skilled personnel for its application. This means that continuous disinfection can take place in dynamic environments during periods of high activity, and hence high bacterial transmission. Because intracellular photosensitive molecules exist within bacteria in different quantities and conformations, different bacterial species are inactivated at slightly different rates. Consequently, continuous disinfection is particularly advantageous.

The lighting device of the invention lends itself to easy installation, and can be readily incorporated into new and existing ambient lighting arrangements. Because of this it can be used in many different environments such as nursing homes, prisons, gymnasiums, health clubs, restaurants, retail outlets, and homes, particularly where bacterial levels might be above average, as in changing rooms, bathrooms, toilets and kitchens. The lighting device may be fixed in position, for example, somewhere around ceiling height—perhaps as part of the ambient lighting—in order to illuminate a chosen region, or it may take the form of desk lighting. Alternatively, it may be on a mobile unit that can be optimally positioned. In any given (indoor) environment, more than one of the devices may be installed in order to provide near-uniform irradiance over a large area. The light outputs and positions of the lighting devices may be configured to provide HINS-light irradiance over the chosen area that is within the safety guidelines. Knowledge of the irradiance pattern of a single device allows computation of the pattern of irradiance for any given configuration of devices.

A skilled person will appreciate that variations of the disclosed arrangements are possible without departing from the scope of the invention. Accordingly the above description of the specific embodiment is made by way of example only and not for the purposes of limitations. It will be clear to the skilled person that minor modifications may be made without significant changes to the operation described.

The invention claimed is:

1. A lighting device with at least one first-element that emits visible light at a wavelength and irradiance sufficient to inactivate one or more pathogenic bacterial species, and at least one second element that emits light of one or more longer wavelengths to that of the first-element, wherein the at least one second element has a higher illuminance than that of the at least one first element.

2. A lighting device as claimed in claim 1, wherein the at least one second element has an illuminance that is at least two times the illuminance of the at least one first element.

3. A light device as claimed in claim 1, wherein the combined output is white or a shade of white.

4. A lighting device with at least one first-element that emits visible light at a wavelength and intensity sufficient to inactivate one or more pathogenic bacterial species, and at least one second-element that emits light of one or more different wavelengths to that of the first-element, wherein the at least one first, bacteria inactivating, element and at least one second element are such that the combined output of the light source is white or a shade of white.

5. A device as claimed in claim 1, wherein the at least one first element is operable in a first mode to emit light having an irradiance in a first range, and in a second mode to emit light having an irradiance in a second, different range.

6. A lighting device with at least one first-element that emits visible light at a wavelength and intensity sufficient to inactivate one or more pathogenic bacterial species in the air and on contact surfaces and materials, and at least one second-element that emits light of different wavelengths to that of the first-element, wherein the at least one first element is operable in a first mode to emit light having an irradiance in a first range, and in a second mode to emit light having an irradiance in a second, different range.

7. A device as claimed in claim 1, wherein each element is a light emitting diode (LED).

8. A device as claimed in claim 1, wherein the device is incorporated into existing lighting systems.

9. A device as claimed in claim 1, wherein the at least one first-element emits bacteria-inactivating light at a wavelength in the range 380 nm to 420 nm.

10. A device as claimed in claim 9 wherein the wavelength of the bacteria-inactivating light is centred on 405 nm.

11. A device as claimed in claim 1, wherein the at least one second-element emits white light or light of any wavelength within the visible spectrum.

12. A device as claimed in claim 1, comprising a lens for directing light onto a particular region.

13. A device as claimed in claim 1, comprising a diffuser for blending light from the first-element and the second-element.

14. A device as claimed in claim 1, wherein there is a plurality of first elements.

15. A device as claimed in claim 1, wherein there is a plurality of second-elements.

16. A device as claimed in claim 1, wherein the or each second-element emits white light.

17. A device as claimed in claim 1, wherein the at least one first element is operable to emit light that irradiates surrounding surfaces with an irradiance in the range up to 0.50 $mW/cm^2$.

18. A device as claimed in claim 5, wherein the light emitted in the second mode has an irradiance that is greater than that in the first mode.

19. A device as claimed in claim 5, wherein light emitted in the first mode has an irradiance in the range up to 0.50 $mW/cm^2$.

20. A device as claimed in claim 5, wherein the light emitted in the second mode has an irradiance in a range that is greater than that in the first mode.

21. A device as claimed in claim 5, comprising means for switching between the first and second modes.

22. A device as claimed in claim 21 wherein the means for switching is responsive to detection of a person.

23. A device as claimed in claim 21 wherein the means for switching is responsive to detection of movement.

24. A device as claimed in claim 21 wherein the means for switching is responsive to detection of a change in an environment.

25. A device as claimed in claim 1, comprising means for varying the level of irradiance.

26. A device as claimed in claim 1, comprising means for switching between different fixed levels of irradiance.

27. A device as claimed in claim 1, adapted for use as a wall or roof light.

28. A device as claimed in claim 1, adapted for use as lighting for an enclosure.

29. A device as claimed in claim 1, adapted for use for environmental lighting.

30. A lighting device with at least one first-element that emits visible light at a wavelength and intensity sufficient to inactivate one or more pathogenic bacterial species, and at least one second-element that emits light of different wavelengths to that of the first-element, wherein the at least one second element is operable to provide environmental illumination.

* * * * *